United States Patent [19]
Andrade et al.

[11] Patent Number: 4,668,795
[45] Date of Patent: May 26, 1987

[54] PROCESS FOR THE PRODUCTION OF OPTICALLY ACTIVE 1-BENZYL-3,4-BIS-(DIPHENYLPHOSPHINO)-PYRROLIDINE

[75] Inventors: Juan G. Andrade, Kleinostheim; Günter Prescher, Hanau; Ulrich Nagel, Weichs, all of Fed. Rep. of Germany

[73] Assignee: Degussa Aktiengesellschaft, Frankfurt am Main, Fed. Rep. of Germany

[21] Appl. No.: 804,470

[22] Filed: Dec. 4, 1985

[30] Foreign Application Priority Data

Dec. 19, 1984 [DE] Fed. Rep. of Germany ....... 3446303

[51] Int. Cl.$^4$ ................................................. C07F 9/65
[52] U.S. Cl. .................................... 548/412; 548/402
[58] Field of Search ................................ 548/412, 402

[56] References Cited

U.S. PATENT DOCUMENTS 4,424,312 1/1984 Stille ............................... 548/412 X
4,539,411 9/1985 Broger et al. ...................... 548/402

FOREIGN PATENT DOCUMENTS 3302697 8/1983 Fed. Rep. of Germany ...... 548/402

OTHER PUBLICATIONS

Bourson, et al., J. Organometallic Chem., vol. 229, pp. 77–84 (1982).
Nagel, Angew. Chem. Int. Ed. Engl., vol. 23, No. 6, pp. 435–436 (06/84).

Primary Examiner—Donald G. Daus
Assistant Examiner—Diana G. Rivers
Attorney, Agent, or Firm—Cushman, Darby & Cushman

[57] ABSTRACT

Optically active 1-benzyl-3,4-bis-(diphenylphosphino)-pyrrolidine is produced in a three-step process from optically active 1-benzyl-2,5-dioxo-3,4-dihydroxy-pyrrolidine. The product is useful as a chiral ligand in rhodium complexes which serve as catalysts for the homogeneous asymmetric hydrogenation of prochiral substrates.

16 Claims, No Drawings

PROCESS FOR THE PRODUCTION OF OPTICALLY ACTIVE 1-BENZYL-3,4-BIS-(DIPHENYLPHOSPHINO)-PYRROLIDINE

BACKGROUND OF THE INVENTION

The invention is directed to a process for the production of optically active 1-benzyl-3,4-bis(diphenylphosphino)-pyrrolidine of the formula

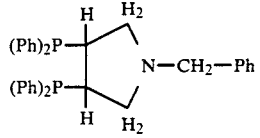

in which Ph indicates a phenyl group.

This pyrrolidine derivative is described in old, not yet published German application P3403194.4 published Aug. 1, 1985 as German OS No. P3403194 (and the related Beck U.S. application Ser. No. 688,360 filed Jan. 2, 1985, the entire disclosure of which is hereby incorporated by reference and relied upon) as a chiral ligand in rhodium complexes, and there is also described the use of the rhodium complexes as catalysts for the homogeneous hydrogenation of unsubstituted or β-substituted α-acylamino acrylic acids. The process for the production of the pyrrolidine derivative also described in the above-mentioned German application and Beck U.S. application requires an extraordinarily large number of steps and consequently is quite cumbersome and protracted.

There has now been found a new process for the production of the compound 1-benzyl-3,4-bis(diphenylphosphino)-pyrrolidine in only three proces steps in a relative simple manner.

SUMMARY OF THE INVENTION

The process of the invention comprises:

(a) reducing optically active 1-benzyl-2,5-dioxo-3,4-dihydroxy-pyrrolidine of the formula:

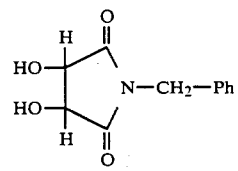

at a temperature between −50° and +170° C. in an inert solvent and in the presence of 0.1 to 20 times the molar amount of boron trifluoride with 1 to 20 times the molar amount of sodium borohydride to 1-benzyl-3,4-dihydroxy-pyrrolidine

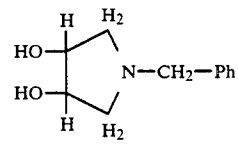

(b) converting this compound at a temperature between −40° and +100° C. in the presence of 2 to 20 times the molar amount of a tertiary amine with 2 to 10 equivalents of methanesulfonic acid anhydride or chloride into 1-benzyl-3,4-dimethanesulfonyl-pyrrolidine of the formula:

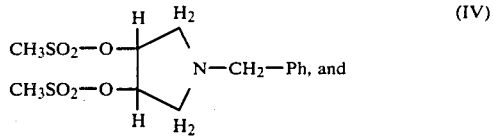

(c) reacting this compound at a temperature between −20° and +40° C. in an inert solvent and with the exclusion of oxygen with 2 to 6 times the molar amount of alkali metal diphenylphosphide.

The optically active 1-benzyl-2,5-dioxo-3,4-dihydroxy-pyrrolidine of formula (II) serving as starting material in process step (a) can be produced in a simple manner known of itself by condensing optically active tartaric acid with benzylamine. If there is employed thereby L-tartaric acid, the end product of the process of the invention is 1-benzyl-3,4-(R,R)-bis(diphenylphosphino)-pyrrolidine, if the starting material is D-tartaric acid then in a corresponding manner there is formed 1-benzyl-3,4-(S,S-bis(diphenyl-phosphino)-pyrrolidine.

Process step (a) is preferably carried out at a temperature between 0° and 100° C. Suitable inert solvents are those in which boron trifluoride ($BF_3$) and sodium borohydride ($NaBH_4$) are soluble, such as diethyl ether, diisopropyl ether, 1,4-dimethoxybutane, tetrahydrofuran or diethyleneglycol dimethyl ether. The boron trifluoride can be employed as a gas or as an etherate complex. It is preferably used in 1 to 6 times the molar amount of the compound of formula (II). The sodium borohydride is suitably added slowly in small portions with ice cooling. It is used preferably in 1 to 4 times the molar amount of the compound of formula (II).

Working up the crude reaction mixture of process step (a), for example, can be carried out in such manner that excess hydrochloric acid is slowly dropped in until the development of gas ends and then again heating for a short time to higher temperature, e.g., 70° C. It is especially advantageous if there is then added a complex former for the boron compound (or compounds) contained in the reaction mixture and the mixture heated again for some time to a higher temperature, e.g., 100° C. Such complex formers, for example, are polyhydroxy compounds having adjacent hydroxyl groups, such as, for example, glycerine, sugar alcohols, e.g., sorbitol, mannitol, xylitol, and arabinitol, or sugars, especially monosaccharides, e.g., glucose, fructose, sorbose, arabinose, galactose, and xylose, and/or alkali metal fluorides, e.g, potassium fluoride and especially sodium fluoride. This material is suitably used in a molar excess over the entire amount of boron compounds employed. After cooling the mixture is then neutralized with aqueous sodium hydroxide. The aqueous phase is separated off and discarded, the organic phase evaporated under reduced pressure. The residue is taken up in water and exhaustively extracted with a suitable solvent, preferably ethyl acetate. The combined extracts are concentrated to the smallest possible volume under reduced pressure and cooled to a lower temperature, e.g., 5° C. Then 1-benzyl-3,4-dihydroxy-pyrrolidine of formula (III) crystallizes upon standing.

Process step (b) is preferably carried out at a temperature between −20° and +20° C. The tertiary amine is suitably employed in the same molar amount as the mesylation agent. Suitable tertiary amines, for example, are tertiary alkylamines such as triethylamine or tris-n-butylamine or pyridine. As mesylation agent, there is preferably used methanesulfonyl chloride. In a given case, the reaction can also be carried out in an inert solvent. Suitable solvents especially are aliphatic hydrocarbons such as n-pentane or n-hexane; methylene chloride or carbon tetrachloride. The mesylation agent is suitably dropped in slowly with cooling to the already present 1-benzyl-3,4-dihydroxy pyrrolidine of formula (III) and the tertiary amine in a given case as a solution in an inert solvent. The mesylation agent as well as the tertiary amine is preferably used in 2 to 4 times the molar amount of the compound of formula (III). After ending the addition of the mesylation agent, it is recommended that stirring of the reaction mixture be continued for about 30 minutes at room temperature or higher.

The working up of the crude reaction mixture of process step (b), for example, can be carried out in such manner that it is next washed with water and after separation off of the wash water treated with vigorous stirring with excess dilute hydrochloric acid. Then the organic phase, e.g., a methylene chloride phase, is decanted off and discarded. The hydrochloric acid water phase is neutralized at about room temperature with aqueous sodium hydroxide and the oily precipitate separating thereby is extracted with methylene chloride. The solvent is evaporated off under reduced pressure and the residue is recrystallized from ethanol.

Process step (c) is preferably carried out at a temperature between $-10°$ and $+10°$ C. Suitable inert solvents, for example, are ethers, such as diethyl ether, di-n-butyl ether, tetrahydrofuran or dioxane. Air oxygen is rigorously excluded by use of an inert gas atmosphere, for example, nitrogen or argon. As alkali metal diphenylphosphide there is preferably used lithium, sodium, or potassium diphenylphosphide. It is preferably employed in 2 or 3 times the molar amount of the compound of formula (IV). Suitably, it is produced freshly in situ from the alkali metal and chlorodiphenylphosphine.

The 1-benzyl-3,4-dimethanesulfonylpyrrolidine is added to the solution of the alkali metal diphenylphosphide present in solution.

The working up of the crude reaction mixture of process step (c), for example, can be carried out in such manner that it is treated with a small amount of water and then it is evaporated under reduced pressure. The residue is taken up in diethyl ether and the ether solution is washed with water which then is discarded. Subsequently, the 1-benzyl-3,4-bis(diphenylphosphino)-pyrrolidine of formula (I) contained in the solution is isolated as the hydrochloride. Furthermore, the ether solution is treated with dilute hydrochloric acid, whereby there is formed a waxy precipitate. The liquid phase is decanted off and the residue recrystallized from isopropyl alcohol.

The hydrochloride is very stable in the dry condition. In case it is necessary, the free base can be obtained therefrom by treatment with an alkali metal hydroxide, bicarbonate or carbonate, e.g., sodium hydroxide, potassium hydroxide, sodium bicarbonate, potassium bicarbonate, sodium carbonate, or potassium carbonate or with a tertiary amine, e.g., triethylamine, tributylamine or pyridine.

The invention is illustrated in more detail in the following example for the case of the production of 1-benzyl-3,4-(R,R)-bis(diphenylphosphino)-pyrrolidine hydrochloride from 1-benzyl-2,5-dioxo-3,4-(R,R)-dihydroxypyrrolidine. All percentage data, unless otherwise stated, are weight percent.

The process can comprise, consist essentially of, or consist of the stated steps with the recited materials.

DETAILED DESCRIPTION

Example

Process Step (a)

200 grams (2.94 moles) of gaseous boron trifluoride at 0° C. were led into 1500 ml diethylene glycol dimethyl ether. The solution was treated with 165 grams (0.76 mole) of 1-benzyl-2,5-dioxo-3,4-(R,R)-dihydroxy-pyrrolidine and with ice cooling there were added slowly in small portions 75 grams (2.0 moles) of $NaBH_4$, as a result of which there was an exothermic reaction with the development of gas. After the end of the addition, the reaction mixture was held at 70° C. for a further two hours with stirring and then cooled to room temperature.

Subsequently, 900 ml of 20% hydrochloric acid were dropped in slowly with development of gas and the reaction mixture was heated again for 15 minutes at 70° C. with stirring. Then with stirring there were added all at once 400 grams of sodium fluoride and the reaction mixture was heated at 100° C. for a further 30 minutes. After cooling to 20° C., the reaction mixture was neutralized with 950 ml of 20% aqueous sodium hydroxide. The aqueous phase was separated off and discarded, the organic phase evaporated under reduced pressure. The residue was taken up in 600 ml water and the solution extracted three times, each time with 600 ml of ethyl acetate. The combined extracts were concentrated under reduced pressure to a volume of 500 ml, cooled to 5° C. and allowed to stand overnight at this temperature. There were formed 125.4 grams (87% of theory) of nearly colorless crystals of 1-benzyl-3,4-(S,S)-dihydroxy-pyrrolidine having a melting point of 100° C.

$[\alpha]_D^{20}$: $+32.3°$ (c=1.5; methanol).

Process Step (b)

77 grams (0.4 mole) of 1-benzyl-3,4-(S,S)-dihydroxypyrrolidine and 90 grams (0.88 mole) of triethylamine were dissolved in 500 ml of methylene chloride. There were slowly dropped into the solution at 5° to 10° C. 100.8 grams (0.88 mole) of methanesulfonyl chloride, the reaction mixture was allowed to come to room temperature and stirred for 30 minutes more.

Then the reaction mixture was washed twice, each time with 150 ml of water and the wash water discarded. The methylene chloride solution was stirred vigorously with 2 liters of 1N HCl, subsequently the methylene chloride was decanted off and discarded. The water phase was neutralized at room temperature with 20% aqueous sodium hydroxide. The oily precipitate formed was extracted twice, each time with 300 of methylene chloride. The methylene chloride was evaporated off from the combined extracts under reduced pressure and the residue was recrystallized from 200 ml of ethanol. There were obtained 119 grams (85% of theory) of 1-benzyl-3,4-(S,S)-dimethanesulfonylpyrrolidine having a melting point of 56.5° C.

$[\alpha]_D^{20}$: $+36.4°$ (c=1; methanol).

Process step (c)

Up to the later addition of water the entire reaction was carried out under an argon atmosphere.

25 grams of sodium were suspended as small pieces in 320 ml of absolute dioxane at 20° C. and the suspension heated to reflux temperature. Within about 45 minutes, there were slowly dropped in 66 grams of chlorodiphenyl-phosphine and the reaction was held for a further 2 hours at reflux temperature. Then the mixture was cooled to 80° C. and diluted with 450 ml of absolute tetrahydrofuran. In order to remove the excess sodium, the reaction mixture was filtered over a column filled with glass wool and the filtrate cooled to 0° C.

Then there were added all at once with stirring 41.9 grams of 1-benzyl-3,4-(S,S)-dimethanesulfonyl-pyrrolidine. After standing for one hour, the now gel-like and only difficultly stirrable reaction mixture was diluted with a further 300 ml of absolute tetrahydrofuran and allowed to stand overnight in order to come to room temperature.

After addition of 100 ml of water, the mixture was then evaporated under reduced pressure at a bath temperature of 25° C. The residue was taken up in 350 ml of diethyl ether, washed twice, each time with 100 ml of water, which was then discarded, and treated with 60 ml of 2N HCl, as a result of which a waxy precipitate formed. The liquid phase was decanted off and the residue was recrystallized from 170 ml of isopropyl alcohol. There were obtained 30.8 grams (45.3% of theory) of 1-benzyl-3,4-(R,R)-bis-(diphenylphosphino)-pyrrolidine hydrochloride having a melting point of 102° to 108° C.

$[\alpha]_D^{20}$: +86.9° (c=0.88; methanol).

The entire disclosure of German priority application No. P3446303.8 is hereby incorporated by reference.

What is claimed is:

1. A process of preparing optically active 1-benzyl-3,4-bis(diphenylphosphino)-pyrrolidine of the formula

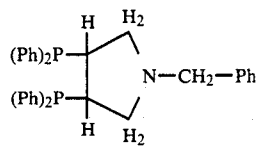

in which Ph is a phenyl group comprising
    (a) reducing optically active 1-benzyl-2,5-dioxo-3,4-dihydroxy-pyrrolidine of the formula:

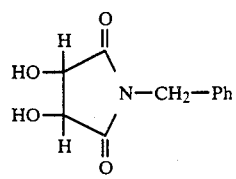

at a temperature between −50° and +170° C. in an inert solvent and in the presence of 0.1 to 20 times the molar amount of boron trifluoride with 1 1 to 20 times the molar amount of sodium borohydride to 1-benzyl-3,4-dihydroxy-pyrrolidine

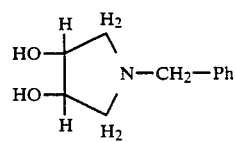

(b) converting this compound into 1-benzyl-3,4-dimethanesulfonyl-pyrrolidine of the formula:

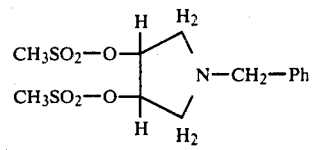

by reacting at a temperature between −40° and +100° C. with 2 to 10 equivalents of methanesulfonic acid anhydride or chloride in the presence of 2 to 20 times the molar amount of a tertiary amine, and (c) reacting compound (IV) at a temperature between −20° and +40° C. in an inert solvent and with the exclusion of oxygen with 2 to 6 times the molar amount of alkali metal diphenylphosphide.

2. A process according to claim 1 comprising carrying out step (a) at a temperature between 0° and 100° C.

3. A process according to claim 2 wherein in step (a) the boron trifluoride is used in 1 to 6 times the molar amount of the compound of formula (II).

4. A process according to claim 1 wherein in step (a) the boron trifluoride is used in 1 to 6 times the molar amount of the compound of formula (II).

5. A process according to claim 3 wherein in step (a) the sodium borohydride is used in 1 to 4 the molar amount of the compound of formula (II).

6. A process according to claim 1 wherein in step (a) the boron trifluoride is used in 1 to 4 times the molar amount of the compound of formula (II).

7. A process according to claim 5 comprising carrying out step (b) at a temperature between −20° and +20° C.

8. A process according to claim 1 comprising carrying out step (b) at a temperature between −20° and +20° C.

9. A process according to claim 7 wherein in step (b) the tertiary amine is used in 2 to 4 times the molar amount of the compound of formula (III).

10. A process according to claim 1 wherein in step (b) the tertiary amine is used in 2 to 4 times the molar amount of the compound of formula (III).

11. A process according to claim 9 wherein in step (b) the methanesulfonic acid anhydride or chloride is used in an amount of 2 to 4 equivalents of the compound of formula (III).

12. A process according to claim 1 wherein in step (b) the methanesulfonic acid anhydride or chloride is used in an amount of 2 to 4 equivalents of the compound of formula (III).

13. A process according to claim 11 comprising carrying out step (c) at a temperature between −20° and +10° C.

14. A process according to claim 1 comprising carrying out step (c) at a temperature between −20° and +10° C.

15. A process according to claim 13 wherein in step (c) the alkali metal diphenylphosphide is used in an amount of 2 to 3 times the molar amount of the compound of formula (IV).

16. A process according to claim 1 wherein in step (c) the alkali metal diphenylphosphide is used in an amount of 2 to 3 times the molar amount of the compound of formula (IV).

* * * * *